United States Patent
Mihan et al.

(10) Patent No.: US 7,081,557 B2
(45) Date of Patent: Jul. 25, 2006

(54) METHOD FOR THE OLIGOMERIZATION OF OLEFINS USING A CYCLOALKYLALKYL-SUBSTITUTED TRIAZACYCLOHEXANE

(75) Inventors: Shahram Mihan, Bad Soden (DE); Ferenc Molnar, Speyer (DE); Heiko Maas, Mannheim (DE); Martina Egen, Dossenheim (DE); Randolf Köhn, Bath (GB)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/507,514

(22) PCT Filed: Mar. 10, 2003

(86) PCT No.: PCT/EP03/02425

§ 371 (c)(1),
(2), (4) Date: Jun. 6, 2005

(87) PCT Pub. No.: WO03/076367

PCT Pub. Date: Sep. 18, 2003

(65) Prior Publication Data

US 2005/0256357 A1 Nov. 17, 2005

(30) Foreign Application Priority Data

Mar. 14, 2002 (DE) .................................. 102 11 386

(51) Int. Cl.
*C07C 2/02* (2006.01)
*C07C 2/24* (2006.01)
*C08F 4/02* (2006.01)

(52) U.S. Cl. .............. 585/513; 585/523; 585/525; 585/526; 585/527; 502/117; 502/123; 502/124

(58) Field of Classification Search .......... 585/513, 585/523, 525–527; 502/117, 123, 124
See application file for complete search history.

(56) References Cited

U.S. PATENT DOCUMENTS

| 4,404,344 | A | 9/1983 | Sinn et al. ................ 526/16 |
| 6,844,290 | B1 * | 1/2005 | Maas et al. ............... 502/167 |
| 6,887,958 | B1 * | 5/2005 | Mihan et al. ............. 526/161 |

FOREIGN PATENT DOCUMENTS

| DE | 3007725 | 9/1981 |
| EP | 0426638 | 5/1991 |
| EP | 0468537 | 1/1992 |
| JP | 10231317 | 9/1998 |
| WO | 0034211 | 6/2000 |
| WO | 0058319 | 10/2000 |

OTHER PUBLICATIONS

W. A. Hermann et al., "Synthetic Methods of Organometallic and Inorganic Chemistry," vol. 1, Literature, Laboratory Techniques and Common Starting Materials; *Thieme Medical Publishers,Inc.*, New York (1996 Georg Theime Verlag, Rüdigerstrasse 14, D-70469 Stuttgart); Printed in Germany by Gutmann & Co GmbH, D-74388 Talheim.

Randolf D. Köhn et al., "Selective Trimerization of α-Olefins with Triazacyclohexane Complexes of Chromium as Catalysts;" *Angewandte Chemie, International Edition, Verlag Chemie*, Weinheim, Germany; vol. 39(23), p. 4337-4339 (2000).

* cited by examiner

*Primary Examiner*—Walter D. Griffin
*Assistant Examiner*—In Suk Bullock

(57) ABSTRACT

Disclosed is a method for the oligomerization of olefins, wherein an olefin is brought into contact with a catalyst system that is obtained from a chromium source, a cycloalkylalkyl-substituted triazacyclohexane, especially a 1,3,5-tris-(cycloalkylalkyl)-1,3,5-triazacyclohexane and an activator such as an alkyl aluminum compound or an alkylalumoxane.

9 Claims, No Drawings

METHOD FOR THE OLIGOMERIZATION OF OLEFINS USING A CYCLOALKYLALKYL-SUBSTITUTED TRIAZACYCLOHEXANE

This application is the U.S. national phase of International Application PCT/EP03/02425, filed Mar. 10, 2003.

The present invention relates to a process for the oligomerization of olefins and to a catalyst system suitable for this purpose.

Olefin oligomers having up to 30 carbon atoms are of great economic importance as comonomers for plastics or as precursors of oxo alcohols which are in turn constituents of surfactants and plasticizers for plastics. Processes for the oligomerization of lower olefins which are obtained, for example, from steam crackers are thus of key importance in the production of products encountered in daily life.

WO 00/58319 describes a process for preparing oligomers of olefins using an oligomerization catalyst which is obtainable from a chromium compound and a 1,3,5-triazacyclohexane together with an activating additive.

JP-A-10/231317 discloses a process for preparing a-olefin polymers using a vanadium or chromium complex, a polydentate nitrogen compound and an alkylaluminum compound.

It is an object of the present invention to provide a process of the type mentioned at the outset which gives high yields of olefin oligomers and preferably displays a high selectivity to defined oligomers, in particular trimers.

We have found that this object is achieved by a process for the oligomerization of olefins in which an olefin is brought into contact with a catalyst system which is obtainable from a) at least one chromium source,
b) at least one ligand of the formula I

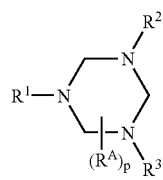

I where $R^1$ to $R^3$ are each, independently of one another, a radical of the formula II

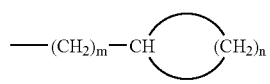

II $$—(CH_2)_m—CH\phantom{...}(CH_2)_n$$

or $C_1$- to $C_8$-alkyl, $R^A$ are each, independently of one another, an organic group having from 1 to 30 carbon atoms which is bound via a silicon atom or a carbon atom, with the proviso that at least one of the radicals $R^1$, $R^2$, $R^3$ and $R^A$ is a radical of the formula II, p is from 0 to 6, preferably from 0 to 3,
m is from 1 to 6, preferably from 1 to 4,
n is from 2 to 6, preferably from 3 to 5, and c) at least one activator.

The invention also provides the catalyst system defined above.

In preferred embodiments, $R^1$ to $R^3$ are, independently of one another, radicals of the formula II and p is 0, or the radicals $R^A$ are radicals other than radicals of the formula II if p is different from 0.

In alternative preferred embodiments, p is different from 0 and the radicals $R^A$ are radicals of the formula II. In particular, p is then 3 and the radicals $R^A$ are arranged symmetrically on the triazacyclohexane ring, i.e. each carbon atom of the triazocyclohexane ring bears one radical $R^A$. In this case, $R^1$ to $R^3$ are preferably each $C_1$–$C_8$-alkyl, in particular methyl or ethyl.

It is preferred that $R^1$ to $R^3$ are each, independently of one another, cyclohexyl-$C_1$–$C_4$-alkyl, in particular cyclohexylmethyl, with p preferably being 0.

If $R^A$ is not a radical of the formula I, this radical is, for example, $C_1$–$C_{18}$-alkyl, preferably $C_1$–$C_{12}$-alkyl such as methyl, ethyl, n-propyl, i-propyl, butyl, pentyl, hexyl; $C_5$–$C_7$-cycloalkyl, such as cyclopentyl and cyclohexyl, $C_6$–$C_{15}$-aryl such as phenyl, methylphenyl or naphthyl; or $C_7$–$C_{15}$-arylalkyl, such as benzyl. Possible radicals $R^A$ bound via a silicon atom are, for example, trialkylsilyl groups such as trimethylsilyl.

Preferred ligands of the formula I are 1,3,5-tri(cyclohexylmethyl)-1,3,5-triazacyclohexane, 1,3,5-tri(cyclohexylethyl)-1,3,5-triazacyclohexane and 1,3,5-tri(cyclohexylpropyl)-1,3,5-triazacyclohexane.

The ligands of the formula I in which p is 0 and the radicals $R^1$ to $R^3$ are identical can be prepared in a manner known per se, in particular by reacting primary amines with formaldehyde or paraformaldehyde. Similarly, ligands of the formula I which bear radicals $R^A$ on the carbon atoms of the triazacyclohexane ring are obtainable from primary amines and appropriate aldehydes and/or ketones. Suitable preparative methods may be found in WO 00/58319 and the references cited therein. The processes described can be employed analogously for the preparation of the ligands of the formula I.

Suitable chromium sources are chromium(II) and/or preferably chromium(III) compounds. Suitable chromium(III) compounds are, in particular, those of the formula $CrX_3$, where X is an abstractable counterion, in particular halogen such as fluorine, bromine, iodine and in particular chlorine; tosylate, triflate, tetrafluoroborate, hexafluorophosphate, hexafluoroantimonate, tetraphenylborate; $C_1$–$C_{18}$-carboxylate such as acetate, butyrate, neopentanoate, laurate, stearate or 2-ethylhexanoate. $CrCl_3$ has been found to be particularly useful.

Further suitable chromium sources are compounds of the formula $CrX_3L_3$, where X is as defined above and L is an uncharged complexing ligand, e.g. ether complexes such as $CrCl_3(tetrahydrofuran)_3$, $CrCl_3(dioxane)_3$, ester complexes such as $CrCl_3(n-butyl\ acetate)$, $CrCl_3(ethyl\ acetate)$, alcohol complexes such as $CrCl_3(i-propanol)_3$, $CrCl_3(2-ethylhexanol)_3$, amine complexes such as $CrCl_3(pyridine)_3$, $CrCl_3(i-propylamine)_3$, or nitrile complexes such as $CrCl_3(acetonitrile)_3$.

The chromium source and the ligand of the formula I can be converted by methods known per se (c.f., for example, W. A. Herrmann, A. Salzer: "*Synthetic Methods of Organometallic and Inorganic Chemistry*" Vol. 1, Thieme Verlag, Stuttgart, 1996) into a chromium complex which is isolated and used in the process of the present invention. As an alternative, the chromium source and the ligand of the formula I are brought into contact in situ in the reaction medium. The ligand of the formula I is generally used in an at least equimolar amount, based on the chromium source (calculated as chromium atoms).

Possible activators are, in particular, metal compounds having at least one metal-carbon bond which are, for the purposes of the present patent application, collectively referred to as "metal alkyl compounds". Representative metal alkyl compounds are alkylaluminum compounds, alkylmagnesium compounds, alkylzinc compounds and/or alkyllithium compounds. Among these, preference is given to alkylaluminum compounds. They can have the formulae $AlR_3$, $AlR_2Hal$, $AlRHal_2$, $AlR_2OR'$, $AlRHalOR'$ or $Al_2R_3Hal_3$, where R and R' are each, independently of one another, methyl, ethyl or a straight-chain or branched $C_3$–$C_8$-alkyl group and Hal is a halogen atom such as fluorine, bromine, iodine or in particular chlorine. Representative compounds are trimethylaluminum, triethylaluminum, tri-n-propylaluminum, tri-isopropylaluminum, tributylaluminum, diethylaluminum chloride, diethylaluminum bromide, diethylaluminum ethoxide, diethylaluminum phenoxide and ethylaluminum ethoxide chloride. Preference is given to using aluminum alkyl compounds of the types $AlR_3$ and $AlRHal_2$, with particular preference being given to triethylaluminum or a mixture of triethylaluminum and ethylaluminum dichloride.

The molar ratio of chromium source to aluminum alkyl compound is usually from 1:1 to 1:100, preferably from 1:5 to 1:50.

Further suitable activators are alkylaluminoxanes as are known, for example, from DE-A 3007725. These are products of the partial hydrolysis of aluminum alkyl compounds. Alkylaluminoxanes can occur in the form of linear or cyclic polymers. The effectiveness of the alkylaluminoxanes as activators is independent of their structural nature. The molar ratio of chromium source to alkylaluminoxane (calculated as aluminum atoms) is usually from 1:1 to 1:10 000, preferably 1:1 000.

In a preferred embodiment of the process of the present invention, a substituted or unsubstituted, five-membered aromatic nitrogen-containing heterocycle is used as activator in addition to an aluminum alkyl compound. Suitable five-membered aromatic nitrogen-containing heterocycles have 1, 2, 3 or 4, preferably 1 or 2, nitrogen atoms in the five-membered atomatic ring. The five-membered aromatic nitrogen-containing heterocycles can be substituted on the ring carbons by groups which are inert under the reaction conditions, e.g. alkyl groups, preferably methyl and/or ethyl, or two adjacent carbon atoms of the five-membered aromatic nitrogen-containing heterocycle can be part of a fused-on aromatic carbocyclic system which may in turn bear inert groups. Examples of such nitrogen-containing heterocycles are unsubstituted and substituted pyrroles, pyrazoles, imidazoles, triazoles and tetrazoles, e.g. pyrrole, 2,5-dimethylpyrrole, indole, carbazole, pyrazole, indazole, imidazole, benzimidazole. Preference is given to using pyrroles and, in particular, alkyl-substituted pyrroles, especially 2,5-dimethylpyrrole.

Further suitable cocatalysts which can be additionally used if appropriate are alkyl halides, alkylsilicon halides and Lewis-acid metal halides, preferably n-butyl chloride, n-butyl iodide, trimethylsilyl chloride, trimethylsilyl bromide, tin tetrachloride, germanium chloride and especially n-butyl bromide.

In a further preferred embodiment of the process of the present invention, at least one boron compound is used as activator in addition to an alkylaluminum compound. Suitable boron compounds are, for example, those having electron-withdrawing radicals, e.g. trispentafluorophenylborane, N,N-dimethylanilinium tetrakis(pentafluorophenyl)borate, lithium tetrakis(pentafluorophenyl)borate, tri-n-butylammonium tetrakis(pentafluorophenyl)borate, N,N-dimethylanilinium tetrakis(3,5-bisperfluoromethylphenyl)borate, tri-n-butylammonium tetrakis(3,5-bisperfluoromethylphenyl) borate and tritylium tetrakis(pentafluorophenyl)borate. Such boron compounds are known from EP-A 468 537 and EP-A 426 638. Preference is given to tritylium tetrakis(pentafluorophenyl)borate, trispentafluorophenylborane and in particular, N,N-dimethylanilinium tetrakis(pentafluorophenyl) borate.

The process of the present invention is generally carried out in the liquid phase in a solvent. Suitable solvents are aprotic solvents, e.g. aliphatic saturated hydrocarbons such as butane, pentane, 3-methylpentane, hexane, heptane, 2-methylhexane, octane, cyclohexane, methylcyclohexane, 2,2,4-trimethylpentane, decalin; halogenated hydrocarbons such as dichloroethane; aromatic hydrocarbons such as benzene, toluene, xylene, ethylbenzene, mesitylene, tetralin, or the oligomeric reaction products which are liquid under the reaction conditions, e.g. 1-hexene. These solvents can be used either individually or as mixtures.

The process of the present invention is suitable for the oligomerization, in particular the selective trimerization, of ethene. The process of the present invention is also suitable for the oligomerization, in particular the selective trimerization, of a-olefins having at least three carbon atoms, e.g. 1-propene, 1-butene, 1-hexane, 1-decene. A particularly useful olefin is 1-butene, either alone or in admixture with its isomers as are present, for instance, in raffinate II.

Owing to the tendency of the metal alkyl compounds used as activators to hydrolyze, the process of the present invention is generally carried out with substantial exclusion of moisture. It is preferably carried out under protective gas. Protective gases which can be used are all gases which are chemically inert under the reaction conditions, e.g. nitrogen or argon. In addition, the olefin to be reacted can itself take on the function of the protective gas as long as it has a sufficiently high vapor pressure under the reaction conditions.

The oligomerization is preferably carried out at from 0 to 120° C., in particular from 20 to 110° C. It is carried out at a pressure of from ambient pressure to 120 bar. A particular advantage of the process of the present invention is that it leads to good yields of oligomerization products even at ambient pressure, i.e. atmospheric pressure.

After the reaction is complete, the catalyst system is generally deactivated. Suitable deactivators are, for example, water which may be acidified or lower alcohols. The products of the oligomerization are advantageously purified by distillation. Unreacted starting material can be recovered and returned to the reaction.

The invention is illustrated by the following examples.

EXAMPLES 1 to 5

Atmospheric-pressure Trimerization of Butene

The chromium complexes indicated in table 1 below together with 250 ml of toluene were placed in a 1 liter four-neck flask provided with contact thermometer, stirring, heating mantle and gas inlet tube at 40° C. Methylaluminoxane (MAO) was used in the form of a 1.6 M solution in toluene. The atomic ratio of Cr:Al is indicated in the table. 1-Butene was passed through the light-green/yellow solution obtained after addition of MAO.

The temperature was kept constant at 40° C. for 1 hour. The reaction was stopped by addition of 15 ml of concentrated hydrochloric acid in 50 ml of methanol, and the reaction mixture was stirred for another 15 minutes. 250 ml of methanol were then added and the mixture was stirred for a further 15 minutes. After filtration, the product was washed three times with water and dried over sodium sulfate. The yield and product distribution were determined on the resulting solution by gas chromatography. The results are summarized in table 1 below.

TABLE 1

| Example | Complex | Amount used [μmol] | Atomic ratio of Cr:Al | Yield of dodecene [g] | Activity [kg/(mole of Cr*h)] |
|---|---|---|---|---|---|
| 1* | $(2\text{-EtHex})_3\text{TAC.CrCl}_3$ | 45.7 | 1:350 | 2.08 | 43 |
| 2 | $(\text{CyCH}_2)_3\text{TAC.CrCl}_3$ | 31.5 | 1:350 | 4.63 | 147 |
| 3 | $(\text{CyCH}_2\text{CH}_2)_3\text{TAC.CrCl}_3$ | 44.3 | 1:350 | 3.74 | 84 |
| 4 | $(\text{CyCH}_2\text{CH}_2\text{CH}_2)_3\text{TAC.CrCl}_3$ | 38.1 | 1:350 | 8.43 | 213 |
| 5* | $(\text{t-BuBz})_3\text{TAC.CrCl}_3$ | 35.6 | 1:350 | 8.43 | 24 |

EXAMPLES 6 and 7

Atmospheric-pressure Trimerization of Ethene

The experiments were carried out as described in examples 1 to 5 using ethene in place of 1-butene. The results are summarized in table 2.

TABLE 2

| Example | Complex | Amount used [μmol] | Atomic ratio of Cr:Al |
|---|---|---|---|
| 6* | $(2\text{-EtHex})_3\text{TAC.CrCl}_3$ | 32.6 | 1:350 |
| 7 | $(\text{CyCH}_2)_3\text{TAC.CrCl}_3$ | 33 | 1:350 |

| | Yield [g] | | | | |
|---|---|---|---|---|---|
| Example | $C_6$ | $C_{10}$ | $C_{12}$ | $C_{14}$ | $C_{18}$ | Polymer |
| 6* | 6.9 | 10.0 | — | 2.8 | — | 0.52 |
| 7 | 6.5 | 20.2 | 0.37 | 6.73 | 1.6 | 0.18 |

| | Activity [kg/(mole of Cr*h)] | | | | | | |
|---|---|---|---|---|---|---|---|
| Example | $C_6$ | $C_{10}$ | $C_{12}$ | $C_{14}$ | $C_{18}$ | Polymer | Total |
| 6* | 213 | 307 | — | 71 | — | 16.0 | 607.0 |
| 7 | 197 | 612 | 11.2 | 204 | 48.5 | 5.5 | 1078 |

*= Comparative example 2-(EtHex)$_3$TAC=1,3,5-tris(2-ethylhexyl)-1,3,5-triazacyclohexane
(CyCH$_2$)$_3$TAC=1,3,5-tris(cyclohexylmethyl)-1,3,5-triazacyclohexane
(CyCH$_2$CH$_2$)$_3$TAC=1,3,5-tris(2-cyclohexylethyl)-1,3,5-triazacyclohexane
(CyCH$_2$CH$_2$CH$_2$)$_3$TAC=1,3,5-tris(3-cyclohexylpropyl)-1,3,5-triazacyclohexane
(t-BuBz)$_3$TAC=1,3,5-tris(p-t-butylbenzyl)-1,3,5-triazacyclohexane.

We claim:

1. A process for the oligomerization of olefins in which an olefin is brought into contact with a catalyst system which is obtained from
    a) at least one chromium source;
    b) at least one ligand of the formula I

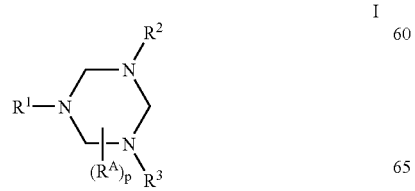

I where $R^1$ to $R^3$ are each, independently of one another, a radical of the formula II

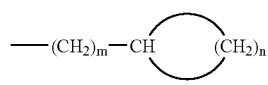

II or $C_1$- to $C_8$-alkyl;
$R^A$ are each, independently of one another, an organic group having from 1 to 30 carbon atoms which is bound via a silicon atom or a carbon atom, with the proviso that at least one of the radicals $R^1$, $R^2$, $R^3$ and $R^A$ is a radical of the formula II;
p is from 0 to 6;
m is from 1 to 6;
n is from 2 to 6; and
c) at least one activator.

2. The process as claimed in claim 1, wherein $R^1$ to $R^3$ are each, independently of one another, cyclohexyl-$C_1$–$C_4$-alkyl.

3. The process as claimed in claim 2, wherein $R^1$ to $R^3$ are each cyclohexylmethyl.

4. The process as claimed in claim 1, wherein p is 3 and the radicals $R^A$ are arranged symmetrically on the triazacyclohexane ring and are, independently of one another, radicals of the formula II.

5. The process as claimed in claim 1, wherein the activator comprises an alkylaluminum compound.

6. The process as claimed in claim 5, wherein the activator is selected from among AlR$_3$, AlR$_2$Hal, AlRHal$_2$, AlR$_2$OR', AlRHalOR' or Al$_2$R$_3$Hal$_3$, where R and R' are each, independently of one another, methyl, ethyl or a straight-chain or branched C$_3$–C$_8$-alkyl group and Hal is a halogen atom, and alkylaluminoxanes.

7. The process as claimed in claim 1, wherein the olefin is ethene.

8. The process as claimed in claim 1, wherein the olefin is an a-olefin having at least 3 carbon atoms.

9. A catalyst system obtained from
    a) at least one chromium source;
    b) at least one ligand of the formula I

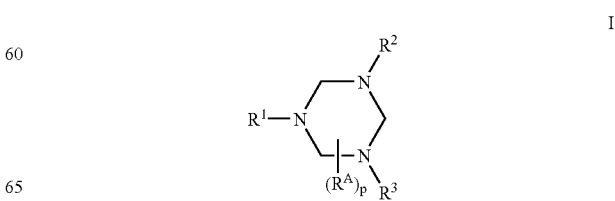

I where $R^1$ to $R^3$ are each, independently of one another, a radical of the formula II

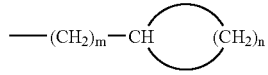   II or $C_1$- to $C_8$-alkyl;

$R^4$ are each, independently of one another, an organic group having from 1 to 30 carbon atoms which is bound a silicon atom or a carbon atom, with the proviso that at least one of the radicals $R^1$, $R^2$, $R^3$ and $R^4$ is a radical of the formula II;

p is from 0 to 6;
m is from 1 to 6;
n is from 2 to 6; and c) at least one activator.

* * * * *